United States Patent [19]

Allen et al.

[11] Patent Number: 5,318,200
[45] Date of Patent: Jun. 7, 1994

[54] EARPLUG DISPENSER

[75] Inventors: James L. Allen, Lake Villa; Walter Herbst, Evanston; Gregory W. Lantz, Wheaton, all of Ill.

[73] Assignee: Cabot Safety Corporation, Southbridge, Mass.

[21] Appl. No.: 891,578

[22] Filed: Jun. 1, 1992

[51] Int. Cl.⁵ ............................................. B65H 3/00
[52] U.S. Cl. .................................. 221/192; 221/254
[58] Field of Search ................ 221/254, 192, 195, 196, 221/281

[56] References Cited

U.S. PATENT DOCUMENTS

| | | |
|---|---|---|
| 672,330 | 4/1901 | Peck . |
| 774,615 | 11/1904 | Tarner . |
| 807,376 | 12/1905 | Hallock . |
| 888,443 | 5/1908 | Kent . |
| 1,049,776 | 1/1913 | Stauffer . |
| 1,354,202 | 9/1920 | Lafleche ............................ 221/254 |
| 1,996,472 | 4/1935 | Hermann . |
| 2,238,725 | 4/1941 | Fry . |
| 2,496,304 | 2/1950 | Muffly . |
| 3,907,135 | 9/1975 | Populin et al. . |
| 4,227,626 | 10/1980 | Merila . |

FOREIGN PATENT DOCUMENTS 1246694  10/1989  Japan .................................. 221/192

Primary Examiner—David H. Bollinger
Attorney, Agent, or Firm—Michelle B. Lando; Harry J. Gwinnell

[57] ABSTRACT

An earplug dispenser to deliver one or two earplugs from a bulk supply which includes a front housing having an access door, a rear housing and a removable cover. Situated inside of the rear housing is a hopper having an opening with a central tab. A chute is located inside the front housing and has a trough which terminates slightly below the lower edge of the access door. A conveyor member, attached to a supporting extrusion member includes a pair of rollers which are journalled one above the other, a belt mounted on the rollers having a series of carriers and a means for rotating the rollers. As the rollers are rotated, the carriers are elevated through the hopper of earplugs picking up an earplug and dispensing it down the chute to the trough. Earplugs are easily removed through the access door.

17 Claims, 3 Drawing Sheets

EARPLUG DISPENSER

BACKGROUND OF THE INVENTION

1. Field of the Invention

The present invention relates to a dispenser for uniformly shaped and randomly oriented articles, and more particularly to a dispenser for earplugs.

2. Description of the Prior Art

Health and safety regulations require that individuals working in noisy environments be protected from that environment by wearing appropriate safety equipment. Various types of hearing protectors are currently available to workers for this purpose, such as earplugs, ear muffs and semi-aural hearing protectors. Earplugs have gained universal acceptance because of their size, comfort and attenuation characteristics.

For sanitary reasons, earplugs are typically available in individual pillow-shaped packages, poly bags and other suitable containers designed to hold a pair of plugs. However, in heavy industrial environments, the plugs often become soiled. Although some commercially available plugs may be washed, this is not always practicable. As a result, there is a need for clean plugs to be readily available to individuals in the work environment.

Known in the art is an earplug dispenser utilizing a strip package of earplugs on a carousel or bandolier reel. In this type of dispenser, the strip of plugs is channelled over and down to an outside tab which catches the strip and detaches one pair of ear plugs at a time.

Although dispensers are presently available for industrial settings, several disadvantages are associated with their use. For example, in the bandolier-type dispenser, only additional reels of the strip earplugs may be used to refill the dispenser. In addition, plugs utilizing a strip packaging will tend to pre-compress before delivery to an actual user. If pre-compressed for any length of time, the plug may not be able to recover to its natural uncompressed state. Improper sealing of the ear canal, thus decreasing of effectiveness of the earplug (i.e. lower attenuation to the user), may therefore result. Finally, excessive waste is associated with these strip packages as well as with individual packages. A need therefore exists for manufacturers to be able to supply earplugs in bulk while maintaining the integrity of the earplugs in a sanitary dispensing operation.

SUMMARY OF THE INVENTION

It is therefore an object of the present invention to provide a dispenser which will reliably dispense one or two earplugs at a time from a large supply to an external station where it may be grasped and removed by the operator. Another object is to provide an earplug dispenser which is simple and inexpensive while providing workers with quick and easy access to the earplugs. Another object is to provide a dispenser which is environmentally sound by minimizing excess paper waste associated with individual and strip packaging.

According to the teaching of the present invention, a dispenser for delivering earplugs is disclosed which includes a front housing having an access door, a rear housing and a removable cover. Situated inside of the rear housing is a hopper having an opening with a central tab. A chute is situated inside of the front housing having a trough which terminates slightly below the lower edge of the access door. An extrusion member is disposed between the rear and front housing to provide support. A conveyor member, also supported by the extrusion member, includes a pair of rollers journalled one above the other, a belt mounted on the rollers having a series of carriers, and a means for rotating the rollers thereby causing the carriers to be elevated through the hopper. In a preferred embodiment, the carriers include a pair of spaced apart finger-like projections having an upward curve.

DETAILED DESCRIPTION OF THE PRESENT INVENTION

Figure 1:
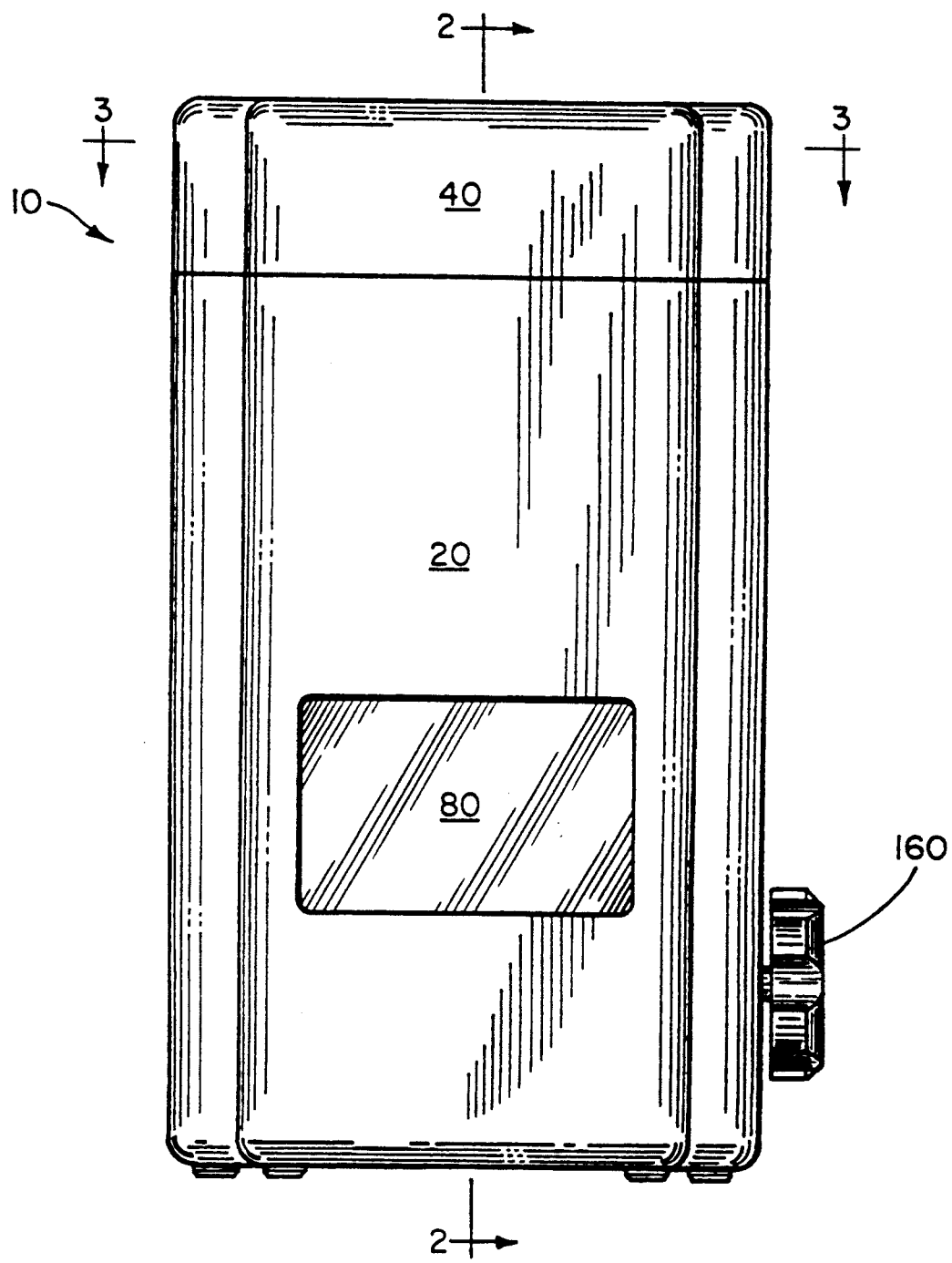
FIG. 1 is a front elevational view of the earplug dispenser in accordance with one embodiment of the present invention.

Referring to the drawings wherein like reference numerals indicate like features, the dispenser 10 of the present invention includes, in one embodiment, a front housing 20, a rear housing 30 and a removable cover 40. Front and rear housings, 20 and 30 respectively, and cover 40 may be constructed from any suitable material such as wood, metal or plastic and may be of any artistic design. Preferred materials are high-impact resistant thermoplastics such as polyvinylchloride, acrylonitrile-butadiene-styrene (abs) resin and other rigid, high density polymers. Cover 40 is readily removable to permit easy access to the interior of the housings. Front housing 20 is provided with an access door 80 at its forward side for removing earplugs from dispenser 10.

Figure 2:
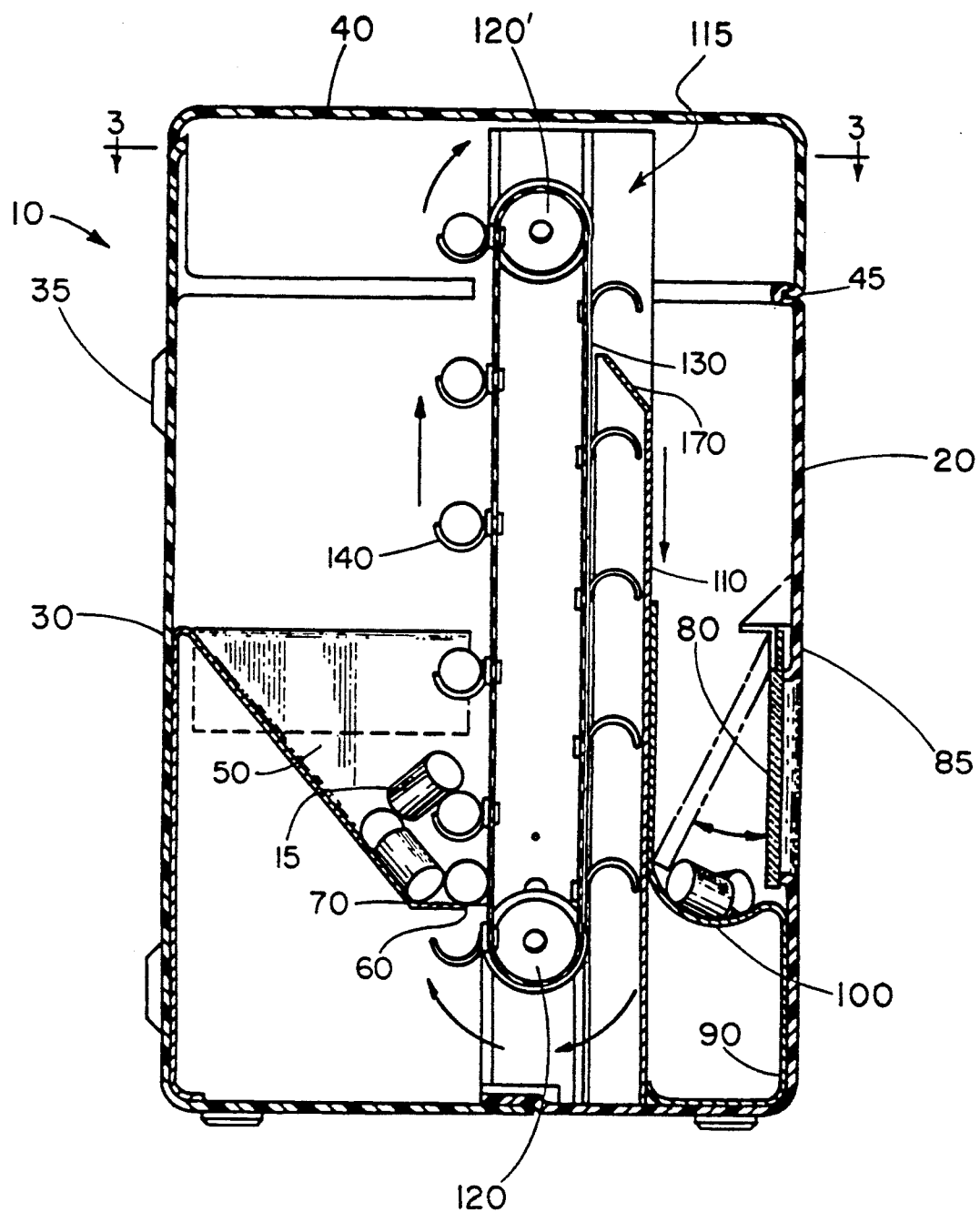
FIG. 2 is a sectional view of the earplug dispenser taken along line II—II of FIG. 1.
Figure 3:
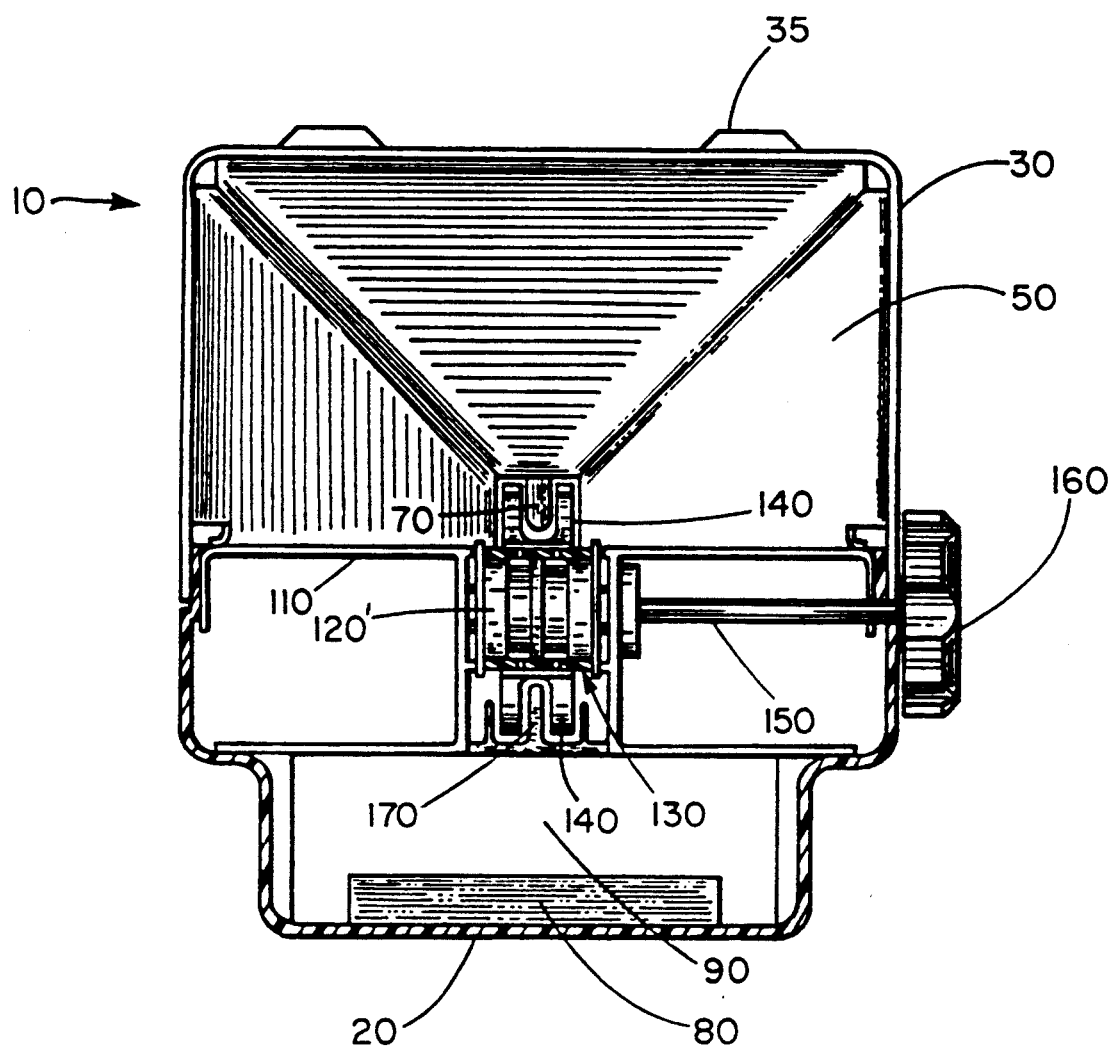
FIG. 3 is a sectional view of the earplug dispenser taken along line III—III of FIG. 1.

Referring now especially to FIGS. 2 and 3, situated inside of rear housing 30 is a rear bin or hopper 50 which retains a quantity of earplugs 15, in a jumbled mass. At the bottom of hopper 50 is an opening 60 having a central tab 70 suitable sized to prevent the earplugs from falling out the bottom of hopper 50. Hopper 50 can be accordingly sized to receive any desired quantity of earplugs. Preferably, hopper 50 is angled from three of its sides to form a funnel in the front portion of rear housing 30. An angle of between about 25° and 45° is preferred because such an angle will tend to move the earplugs down the sloping bottom of hopper 50 toward opening 60.

Situated inside of front housing 20 is a front bin or chute 90 having a cup-like trough 100 which terminates below the lower edge of access door 80. Trough 100 is preferably shallow enough to allow easy user access to facilitate grasping of dispensed earplugs. However, trough 100 should not be too shallow so as interfere with the opening of access door 80 when retaining earplug 15.

Bin 50 and chute 90 may also be constructed from any suitable material such as wood, metal or plastic. Most preferred are materials which are durable, easy to keep clean and smooth, such as stainless steel, aluminum and the like, thereby allowing the plugs to "glide" toward opening 60 and trough 100.

Disposed between rear housing 30 and front housing 20 is extrusion member 110 which serves as a support to the housings, as well as to conveyor mechanism 115 which is designed and adapted to communicate with opening 60, pick-up earplug 15, travel it through the mass of plugs in hopper 50, and discharge it into chute 90. Preferably, extrusion member 110 has an angled portion 170 on the side supporting front housing 20 which is adapted to clear any lodged plugs.

Conveyor mechanism 115 includes a pair of axles or rollers 120 and 120' journalled one above the other, a belt 130 disposed around rollers 120 and 120', and a means 150 for rotating the same. Means 150 is rotated or turned by a knob or handle 160 located on the exterior of dispenser 10 which directly communicates with means 150 to turn belt 130. Means 150 is any conventional assembly such as a gear and axle arrangement or the like which will permit motion of belt 130 when roller 120 is caused to rotate by manipulation of handle 160. Alternatively, means 150 may be electrically or automatically controlled.

Firmly secured to belt 130 by conventional means is a plurality or series of equally spaced carriers 140 closely arranged to each other, each carrier being adapted to pick up an earplug from hopper 50. To facilitate segregation of an earplug from the mass of plugs in hopper 50, in a preferred embodiment, carriers 140 are a pair of spaced apart finger-like projections, each finger-like projection having a gently upward curve. Suitable materials of construction include abs resin, polypropylene, polyethylene and the like. Although the finger-like projections may be specifically tailored to accommodate varying plug designs, finger-like projections having a length between about $\frac{1}{2}$" and $\frac{7}{8}$" and a space therebetween of about $\frac{3}{8}$" and $\frac{1}{2}$" have been found capable of dispensing a variety of plug designs. Most preferred are finger-like projections having a length of about $\frac{7}{8}$" and a space therebetween of about 0.44", such projections having been found to consistently deliver all of the earplugs in hopper 50 while minimizing nesting of the plugs therein.

Opening 60 is of a size and shape to permit finger-like projections of carriers 140 to pass through freely, yet small enough to prevent any earplugs from falling out of the bottom of hopper 50. In the preferred embodiment mentioned above, opening 60 will typically have a length between about 13/16" and $\frac{7}{8}$" and a width of about $\frac{7}{8}$" and $1\frac{1}{8}$". In addition, tab 70 will also prevent earplugs from falling out of hopper 50 and is sized proportionately to fit on finger-like projections as they pass through opening 60.

Access door 80 is preferably connected at its upper end to front housing 20 by any suitable means. Most preferred is a small "living" hinge connection 85 made of polypropylene or the like to permit access door 80 to pivotally swing back and forth between its normal or rest position and its dispensing position (i.e. pushed inward). Access door 80 is of a size and shape to permit easy entry of a user's fingers to grasp dispensed plug 15 from trough 100. Access door 80 is preferably constructed of a transparent glass or plastic material to allow the user to see the number of plugs which have been deposited in trough 100 and prevent excessive dispensing.

Cover 40 is sized proportionately to encase hopper 50, extrusion member 110 and chute 90. A slide-on mechanism of cover 40 is preferred and may be prevented from displacement by a flange 45, situated on the under side of cover 40 and adapted to engage front housing 20 at its upper end which is easily adapted to receive flange 45. Cover 40 may also be provided with other commercially available attachment means such as clips, buckles and the like.

The earplug dispenser of the present invention, in a preferred embodiment, may be used by turning handle 160 on the exterior of dispenser 10 in a predetermined direction. Belt 130 will then begin to turn as handle 160 is manipulated by a worker thereby directing the turning motion through, for example, a gear assembly, to rollers 120 and 120'. As belt 130 turns, carriers 140 move upward through the mass of earplugs in hopper 50 whereby earplug 15 is segregated therefrom. Due to the unique nature of carriers 140, earplug 15 will consistently fit on the finger-like projections and will be securely securely held in place until they are discharged. As carriers 140 pass over the top of roller 120' and head downward through front housing 20, the earplug will drop from the finger-like projections of carrier 140 into chute 90. Carrier 140 will then pass over angled surface 170 to clear the finger-like projections of any lodged earplugs. The earplug is retrieved by a worker by simply pushing access door 80 open and removing the earplug from trough 100. After removing the earplug, access door 80 swings forward to seal trough 100. To load hopper 50 with bulk earplugs, cover 40 is removed from housings 20 and 30 by sliding cover 40 in a forward direction toward front housing 20. Earplugs are directly deposited in bulk to fill hopper 50. Cover 40 is replaced by sliding it in a backward direction toward rear housing 30.

The dispenser can be mounted on a tripod or similar support for convenient counter-top placement. In the alternative, suitable means, for example, key holes 35, hooks and the like may be incorporated into the rear housing for wall hanging.

The present invention provides a dispenser which will reliably dispense one or two earplugs at a time from a large supply to an external station where it may be grasped and removed by an individual operator with a virtually failure-proof and jamb-proof operation. In addition, the earplug dispenser is simple and inexpensive while providing workers with quick and easy access to the earplugs. The earplug dispenser eliminates the need for individual packaging, thus yielding an environmentally sound device which minimizes paper waste.

A non-limiting illustration of the earplug dispenser of the present invention follows:

EXAMPLE

As an example of the above-described principles of the present invention, it has been found that one suitable construction is provided by the following combination of elements.

Front housing 20, rear housing 30 and cover 40 were composed of a pressure formed, high impact abs resin (available from Grimm Brothers Plastics Corporation of Wapello, Iowa) having the following dimensions (in inches):

|  | Front housing 20 | Rear Housing 30 | Cover 40 |
| --- | --- | --- | --- |
| Height | 13.5 | 15.0 | 2.5 |
| Width | 8.5 | 8.5 | 8.5 |
| Depth | 4.5 | 5.5 | 9.0 |
| Starting Thickness | 3/16 | 3/16 | 1/8 |

Four raised pads were molded onto the exterior of rear housing 30, the top two of which had key holes 35 for convenient wall hanging.

Hopper 50 and chute 90 were made of commercially available stainless steel. Hopper 50 had an approximate height of 7.5", a width of 8θ", and a depth of 4¼". From the front vertical, each side of hopper 50 was at an angle of approximately 39°. Opening 60 had a width of about 1" and a depth of about 27/32". Accordingly, tab 70 was ¼" wide and ½" long (deep).

At the point where trough 100 begins at the edge of main extrusion 110 to where it terminates slightly below the lower edge of access door 80, chute 90 had a height of about 4" to 3⅜" high, respectively. Trough 100 was approximately 5¾" wide and has a radius of about 1".

Main extrusion 110 which is made of aluminum grade 6063-T5 (available from Magnode Corporation of Middletown, Ohio) has an overall height, width and depth of about 15⅞", 8" and 2⅜". Supported within main extrusion 110 was conveyor mechanism 115 which used a conventional rubber belt 130, approximately 26" long, and rollers 120 and 120' having a radius of about ⅝". Twelve equally spaced carriers 140 (a distance of 2.167" from each other) were heat staked to belt 130 to provide a secure attachment. Carriers 140 each included a pair of gently curved finger-like projections made of high density polyethylene and having a radius of about 0.31" at its base portion and tapering to approximately 0.041" at its tip portion. Each finger-like projection had a length of ⅝" and a distance of about 0.44" existed therebetween.

Angled portion 170 of main extrusion 110 had a pitch of about 50° and contained three fork-like branches to pass on each side of and in-between the pair of finger-like projections of carrier 140.

Access door 80, made of transparent acrylic available from conventional sources, had a height, width and thickness of approximately, 3⅜", 4¾", and 3/16", respectively. A 4.5×1" polypropylene "living" hinge available from standard sources was used as a swing mechanism while a high performance acrylic adhesive (available from 3M, St. Paul, MN) secured access door 80 to front housing 20.

Finally, means 150 included a conventional gear assembly which permitted motion of belt 130 when roller 120 was caused to rotate by manipulation of handle 160. In the present example, a 36 tooth spur gear having a pitch of 32 and 25 tooth rachet were utilized with a conventional anti-reverse pawl.

Bulk E-A-R ® foam cylindrical earplugs (manufactured by Cabot Safety Corporation, Indianapolis, IN) were deposited in hopper 50. Handle 160 was turned in a clockwise direction, thereby starting and maintaining belt 130 and roller 120 and 120' motion until a pair of earplugs 15 were successively deposited into trough 100. The plugs were easily removed from trough 100 by gently swinging access door 80 open and grasping the plugs. Once removed, access door 80 swung back to its normal resting position.

As illustrated by the above example, the present invention provides a simple, trouble-free mechanism of a sturdy construction which will successively and smoothly dispense the earplugs by manipulation of a handle without jamming or clogging.

It is understood that the present invention is not limited to the particular embodiments shown and described herein, but that various changes and modifications may be made without departing from the scope and spirit of the invention.

What is claimed is:

1. A dispenser for delivering earplugs comprising:
   a front housing having a front housing leg projecting inward from its forward side, a rear housing having a rear housing leg, and a removable cover situated on and encompassing said front and rear housings, wherein said front housing has an access door located on its forward side and said front housing leg and said rear housing leg face towards each other;
   a hopper situated inside of said rear housing, said bottom of said hopper having an opening with a central tab;
   a chute situated inside of said front housing having a trough which terminates below the lower edge of said access door;
   an extrusion member disposed between said rear and front housings to provide support to said housings and a conveyor member; and said conveyor member located within said extrusion member and comprising a pair of rollers journalled one above the other, a belt mounted on said rollers having a series of carriers, and a means for rotating said rollers, wherein said rotation elevates said carriers.

2. The dispenser according to claim 1 wherein said hopper is angled from three of its sides to form a funnel in the front of said rear housing.

3. The dispenser according to claim 2 wherein said angle is between about 25° and 45°.

4. The dispenser according to claim 1 wherein said carriers comprise pairs of spaced apart finger-like projections having an upward curve.

5. The dispenser according to claim 4 wherein said finger-like projections have a length between about ½" and ⅞" and a space therebetween of about ⅜" and ½".

6. The dispenser according to claim 5 wherein said finger-like projections have a length of about ⅝" and a space therebetween of about 0.44".

7. The dispenser according to claim 1 wherein said opening of said hopper has a length between about 13/16" and about ⅞" and a width between about ⅝" and about 1⅛".

8. The dispenser according to claim 1 wherein said access door is connected to said front housing by a living hinge.

9. The dispenser according to claim 8 wherein said hinge is made of polypropylene.

10. The dispenser according to claim 1 wherein said bin is composed of stainless steel.

11. The dispenser according to claim 1 wherein said chute is composed of stainless steel.

12. The dispenser according to claim 1 wherein aid extrusion member has an angled portion inclined from a point at or near said extrusion member to a point at or near said front housing adapted to clear lodged earplugs on said carriers.

13. The dispenser according to claim 12 wherein said angled portion comprises three fork-like branches.

14. A dispenser for delivering earplugs comprising:
   a front housing having a front housing leg projecting inward from its forward side, a rear housing having a rear housing leg, and a removable cover situated on and encompassing said front and rear housings, where said front housing has an access door located on its forward side and said front housing leg and said rear housing leg face towards each other;
   a hopper situated inside of said rear housing, said bottom of said hopper having an opening with a central tab;

a chute situated inside of said front housing having a trough which terminates below the lower edge of said access door;

an extrusion member disposed between said rear and front housings to provide support to aid housings and a conveyor member; and said conveyor member located within said extrusion member and comprising a pair of rollers journalled one above the other, a belt mounted on said rollers having a series of carriers, said carriers comprising pairs of spaced apart finger-like projections having an upward curve, and means for rotating said rollers wherein said rotation elevates said carriers.

15. The dispenser according to claim 14 wherein said angle of said hopper is between about 25° and 45°.

16. The dispenser according to claim 14 wherein said finger-like projections have a length of about ½" and ⅞" and a space therebetween of about ⅜" and ½".

17. The dispenser according to claim 16 wherein said finger-like projections have a length of about ⅞" and a space therebetween of about 0.44".

* * * * *